US006391339B1

(12) United States Patent
Stiekema et al.

(10) Patent No.: US 6,391,339 B1
(45) Date of Patent: *May 21, 2002

(54) USE OF OLIGOSACCHARIDE FOR PREVENTING BLOOD CLOTTING IN EXTRACORPOREAL BLOOD CIRCUITS

(75) Inventors: Jacobus Christianus Johannes Stiekema, Amsterdam (NL); Jean Marc Herbert, Tournefeuille (FR)

(73) Assignee: Akzo Nobel N.V., Arnhem (NL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/424,626
(22) PCT Filed: May 22, 1998
(86) PCT No.: PCT/EP98/03174
  § 371 Date: Nov. 24, 1999
  § 102(e) Date: Nov. 24, 1999
(87) PCT Pub. No.: WO98/53829
  PCT Pub. Date: Dec. 3, 1998

(30) Foreign Application Priority Data

May 27, 1997 (EP) .............................. 97201586

(51) Int. Cl.⁷ ................................ A61K 9/14
(52) U.S. Cl. .................. 424/488; 424/423; 514/54; 514/56; 514/822
(58) Field of Search .............. 514/56, 822, 54; 424/488, 423

(56) References Cited

U.S. PATENT DOCUMENTS 5,417,969 A * 5/1995 Hsu et al. ................. 424/78.27
5,872,110 A * 2/1999 Van Boeckel et al. ........ 514/56

FOREIGN PATENT DOCUMENTS

EP      0 084 999      8/1983

OTHER PUBLICATIONS

Beguin, S., et al. "The Action of a Synthetic Pentasaccharide on Thrombin Generation in Whole Plasma" Thrombosis and Hemostasis, 61 (3) (1989) p. 397–401.
Barrowcliffe, T., et al., "The Effect of Ca2+, phospholipid and Factor V on the anti–(Factor Xa) Activity of Heparin and Its High–Affinity Oligosaccharides" J. Biochem, (1987) 243, p. 31–37.
Eisenberg, P. et al., "Importance of Factor Xa in Determining the Procoagulant Activity of Whole–Blood Clots" J. Clin. Invest. vol. 91, May 1993, p. 1877–1883.
Cadroy et al., Throm Haemost., 70(4):631–635 (1993).
Bernat et al., Fibrinolysis, 10(3):151–157 (1996).
Schiele et al., Circulation, 94(8 supp.):1742 (1996) Abstract No. 4340.
Messmore et al., Crit. Rev. Clin. Lab. Sci., 23(2):77–94 (1986).
Lormeau et al., Throm. and Hemostasis, 74(6):1474–1477 (1995).
Vogel et al., Throm. and Hemostasis, 69(1):29–34 (1993).
Freedman, Michael D., J. Clin. Pharmacol., 32(7):584–591 (1992).

* cited by examiner

Primary Examiner—Thurman K. Page
Assistant Examiner—Liliana Di Nola-Baron
(74) Attorney, Agent, or Firm—William M. Blackstone

(57) ABSTRACT

The invention relates to the use of a certain oligosaccharide for preventing clotting in an extracorporeal blood circuit of a patient undergoing extracorporeal blood treatment.

2 Claims, No Drawings

USE OF OLIGOSACCHARIDE FOR PREVENTING BLOOD CLOTTING IN EXTRACORPOREAL BLOOD CIRCUITS

The invention relates to the use of a certain oligosaccharide for the manufacture of a medicament for preventing blood clotting in extracorporeal blood circuits. Further the invention relates to a pharmeuceutical composition for said use.

Blood clotting in extracorporeal blood circuits needs to be prevented. Otherwise, blood coagulation occurs as soon as blood contacts artificial surfaces. As a remedy, usually unfractionated heparin (UFH) or low molecular weight heparins (LMWH) are used as anticoagulants.

Both UFH and LMWH have an effect on several stages of the blood coagulation cascade, both inhibiting factor Xa and thrombin (factor IIa). Factor Xa catalyzes the generation of thrombin and subsequently thrombin regulates the last step in the coagulation cascade. The prime function of thrombin is the cleavage of fibrinogen to generate fibrin monomers, which form an insoluble gel by cross-linking, thereby initiating thrombus formation. UFH and LMWH have thrombolytic properties, i.e. they induce dissolution of the thrombus formed.

Contrary to UFH and LMWH, some synthetic oligosaccharides, especially oligosaccharides described in EP 84,999 and U.S. Pat. No. 5,378,829, highly selectively inhibit factor Xa via antithrombin III (ATIII) but do not have any activity on thrombin. However, notwithstanding the absence of any capacity to inhibit thrombin or to promote thrombolysis, it appeared that those oligosaccharides inhibit thrombus formation, e.g. as occurring in extracorporeal blood circuits. Thus, surprisingly, it has now been found that a synthetic oligosaccharide which is a selective inhibitor of factor Xa, acting, via antithrombin III, is useful for preventing blood clotting in patients with an extracorporeal blood circuit.

The use of the oligosaccharide according to this invention results in effective and safe inhibition of blood clotting, e.g. in patients undergoing haemodialysis, without increased bleeding risks.

A preferred oligosaccharide for the use according to this invention is the pentasaccharide with the formula methyl O—(2-deoxy-2-sulphoamino-6-O-suplho-α-D-glucopyranosyl)-(1→4)—O—(β-D-glucopyranosyl uronic acid)-(1→4)—O—(2-deoxy-2-sulphoamino- 3,6-di-O-sulpho-α-D-glucopyranosyl)-(1→4)—O—(2-O-sulpho-α-L-idopyranosyl uronic acid)-(1→4)-2-deoxy-2-sulphoamino-6-O-sulpho-α-D-glucopyranoside or a pharmaceutically acceptable salt thereof (i.e. salts with counter-ions like hydrogen or, more preferably, alkali or earth-alkali metal ions, like sodium, calcium, or magnesium), having the structure:

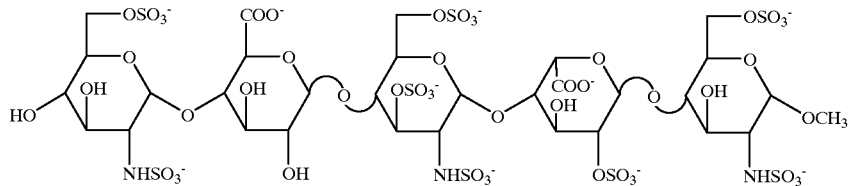

Particularly preferred is its decasodium salt, known by its code name Org 31540 or SR 90107A (described in Chemical Synthesis to Glycosaminoglycans, Supplement to Nature 1991, 350, 30–33).

Other advantageous pentasaccharides are: methyl O—(3, 4-di-O-methyl-2,6-di-O-sulpho-α-D-glucopyranosyl)-(1→4)—O—(3-O-methyl-2-O-sulpho-β-D-glucopyranosyl uronic acid)-(1→4)—O—(2,3,6-tri-O-sulpho-α-D-glucopyranosyl)-(1→4)—O—(3-O-methyl-2-O-sulpho-α-L-idopyranosyl uronic acid)-(1→4)-2,3,6-tri-O-sulpho-α-D-glucopyranoside or a pharmaceutically acceptable salt thereof (especially its dodecasodium salt described in U.S. Pat. No. 5,378,829), having the structure:

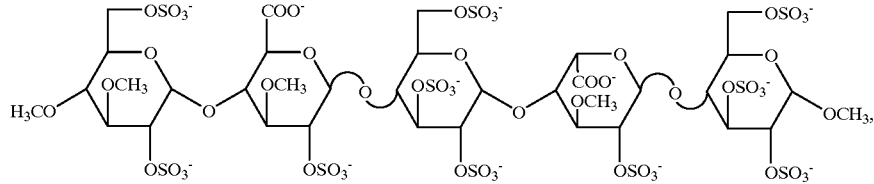

and methyl O—(2,3,4-tri-O-methyl-6-O-sulpho-α-D-glucopyranosyl)-(1→4)—O—(2,3-di-O-methyl-β-D-glucopyranosyl uronic acid)-(1→4)—O—(2,3,6-tri-O-sulpho-α-D-glucopyranosyl)-(1→4)—O—(2,3-di-O-methyl-α-L-idopyranosyl uronic acid)-(1→4)-2,3,6-tri-O-sulpho-α-D-glucopyranoside or a pharmaceutically acceptable salt thereof (especially its nonasodium salt also described in U.S. Pat. No. 5,378,829), having the structure

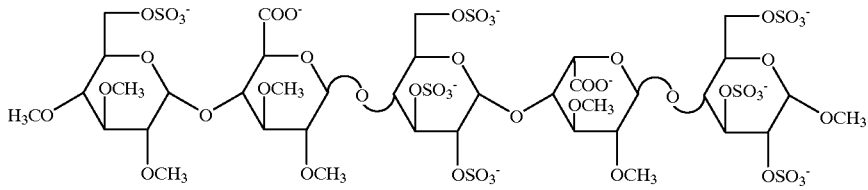

The use in patients with extracorporeal blood circuits according to the invention includes circuits and intravenous infusion lines used for haemodialysis, renal dialysis, haemofiltration, and the like. Preferred extracorporeal circuits are those used in the treatment of haemodialysis patients.

The oligosaccharide can be administered at several stages of the treatment. Preferably, but not limited to this route of administration, the oligosaccharide is administered as an intravenous injection to the mammal undergoing treatment. Preferably, the mammal is a human.

Another route of administration of the oligosaccharide is the introduction thereof into a (dialysis) circuit by other means, e.g. by injecting it either gradually or at once into the system upstream of the dialysis membrane simultaneously with the introduction of the blood into the circuit. Moreover, the lines and/or further equipment of the extracorporeal circuit can be furnished with the oligosaccharide, preferably by way of a coating (but not limited to this). Alternatively, the oligosaccharide may be adsorbed in the materials of parts of the equipment, e.g. in the membranes used for dialysis.

For use according to the invention, the oligosaccharide may be administered enterally or parenterally (especially via the subcutaneous or intravenous route) or may be administered via an external source (vide supra), and for humans preferably in a dosage of 0.001–10 mg per kg body weight per dialysis. More preferably, the pentasaccharide is administered at doses of between 0.30 mg and 30 mg per patient per dialysis.

The oligosaccharide may be used alone or may be presented as a pharmaceutical composition. Accordingly, the present invention further provides a pharmaceutical composition for preventing blood clotting in an extracorporeal blood circuit comprising said oligosaccharide together with pharmaceutically acceptable auxiliaries and optionally other therapeutic agents. The term "acceptable" means being compatible with the other ingredients of the composition and not deleterious to the recipients thereof Compositions include e.g. those suitable for oral, sublingual, subcutaneous, intravenous, intramuscular, transdermal, transmucosal, local, or rectal administration, and the like, all in unit dosage forms for administration.

For oral adminstration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilzed) condition requiring only the addition of sterile liquid carrier, e.g. water, prior to use.

Mixed with such pharmaceutically acceptable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture), the oligosaccharide may be compressed into solid dosage units, such as pills, tablets, or be processed into capsules or suppositories. By means of pharmaceutically acceptable liquids the oligosaccharide can be applied as a fluid composition, e.g. as an injection preparation, in the form of a solution, suspension, emulsion, or as a spray, e.g. a nasal spray.

For use as a coating according to the invention, for example pharmaceutically acceptable polymers may be used as a matrix for the oligosaccharide. Also coatings are included, in which the oligosaccharide is chemically (e.g. covalently) linked to the surface without loss of its activity. Any pharmaceutically acceptable coating may be suitable for this purpose, prepared according to methods conventional in the art.

For making solid dosage units, the use of conventional additives such as fillers, colorants, polymeric binders and the like is contemplated. In general any pharmaceutically acceptable additive which does not interfere with the function of the active compounds can be used. Suitable carriers with which the oligosaccharides of the invention can be administered as solid compositions include lactose, starch, cellulose derivatives and the like, or mixtures thereof, used in suitable amounts. For parenteral administration, aqueous suspensions, isotone saline solutions and sterile injectable solutions may be used, containing pharmaceutically acceptable dispersing agents and/or wetting agents, such as propylene glycol or butylene glycol.

The pharmaceutical composition according to the invention may also be presented in the form of a veterinary composition such compositions may be prepared by methods conventional in the art.

The invention further includes a pharmaceutical composition, as hereinbefore described, in combination with packaging material suitable for said composition, said packaging material including instructions for the use of the composition for the use as hereinbefore described.

The invention is further illustrated by the following example. This should not be considered to be limiting in any way.

EXAMPLE

The pentasaccharide Org 31540/SR 90107 A, as a representative compound for use according to the present invention, has been subject to a pilot clinical study in 12 patients undergoing chronic intermittent haemodialysis.

The study consisted of 2 phases (block A and block B). In block A, 10 mg of Org 31540/SR 90107 A was administered. Thereafter, in block B, 8, 6, and 4 mg of Org 31540/SR 90107 A were used.

Medication was given as an intravenous bolus predialysis for 1 dialysis each week. Efficacy was assessed by determining patency of the dialyzer, buffer and bubble chamber, every hour during dialysis by visual examination and by blood sampling of specific coagualtion, heamatologic and biochemical parameters. Anti-Xa plasma samples, to determine pharmacokinetics, were taken every hour during dialysis and 1 hour after dialysis and daily for 3 days post-dialysis. Safety was assessed by evaluating major and minor bleeding complications each dialysis.

Results: All patients have completed the study. Dialysis could be performed without total clotting of the extracorporeal circuit in all patients for all study dialyses. Only in one patient a clot in the buffer chamber made dialysis impossible half an hour before the end of the last dialysis. No minor or major bleedings were recorded.

Conclusion: The pentasaccharide Org 31540/SR 90107 A is a safe (no increased haemorrhagic risks) and effective (at several doses) anticoagulant to prevent clotting in the extracorporeal blood circuit in haemodialysis patients.

What is claimed is:

1. A method for preventing clotting in an extracorporeal blood circuit of a patient undergoing extracorporeal blood treatment comprising, administering 0.001 to 10 mg of a decasodium salt of methyl O—(2-deoxy-2-sulphoamino-6-O-sulpho-$\alpha$-D-glucopyranosyl)-(1→4)—O—($\beta$D-glucopyranosyl uronic acid)-(1→4)—O—(2-deoxy-2-sulphoamino-3,6-di-O-sulpho-$\alpha$-D-glucopyranosyl)-(1→4)—O—(2-O-sulpho-$\alpha$-L-idopyranosyl uronic acid)-(1→4)-2-deoxy-2-sulphoamino-6-O-sulpho-$\alpha$-D-glucopyranoside per kg body weight of the patient.

2. A method for preventing clotting in an extracorporeal blood circuit of a patient undergoing extracorporeal blood treatment comprising administering 0.30 to 30 mg of a decasodium salt of methyl O—(2-deoxy-2-sulphoamino-6-O-sulpho-$\alpha$-D-glucopyranosyl)-(1→4)—O—($\beta$-D-glucopyranosyl uronic acid)-(1→4)—O—(2-deoxy-2-sulphoamino-3,6-di-O-sulpho-$\alpha$-D-glucopyranosyl)-(1→4)—O—(2-O-sulpho-$\alpha$-L-idopyranosyl uronic acid)-(1→4)-2-deoxy-2-sulphoamino-6-O-sulpho-$\alpha$-D-glucopyranoside.

* * * * *

UNITED STATES PATENT AND TRADEMARK OFFICE
CERTIFICATE OF CORRECTION

PATENT NO. : 6,391,339 B1
DATED : May 21, 2002
INVENTOR(S) : Stiekema et al.

It is certified that error appears in the above-identified patent and that said Letters Patent is hereby corrected as shown below:

<u>Title page,</u>
Item [73], should read:
-- Assignee: Akzo Nobel N.V. (NL) and Sanofi-Synthelabo --

Signed and Sealed this

Twelfth Day of November, 2002

Attest:

Attesting Officer

JAMES E. ROGAN
*Director of the United States Patent and Trademark Office*